United States Patent
Shrivastav

(10) Patent No.: US 11,885,808 B2
(45) Date of Patent: Jan. 30, 2024

(54) PREDICTING PROGNOSIS AND TREATMENT RESPONSE OF BREAST CANCER PATIENTS USING EXPRESSION AND CELLULAR LOCALIZATION OF N-MYRISTOYLTRANSFERASE

(71) Applicant: Canada Inc., Winnipeg (CA)

(72) Inventor: Anuraag Shrivastav, Winnipeg (CA)

(73) Assignee: Oneodrek Inc., Winnipeg (CA)

( * ) Notice: Subject to any disclaimer, the term of this patent is extended or adjusted under 35 U.S.C. 154(b) by 0 days.

(21) Appl. No.: 18/044,172

(22) PCT Filed: May 20, 2022

(86) PCT No.: PCT/CA2022/050808
§ 371 (c)(1),
(2) Date: Mar. 6, 2023

(87) PCT Pub. No.: WO2022/241568
PCT Pub. Date: Nov. 24, 2022

(65) Prior Publication Data
US 2023/0273214 A1    Aug. 31, 2023

Related U.S. Application Data

(60) Provisional application No. 63/190,905, filed on May 20, 2021.

(51) Int. Cl.
| | | |
|---|---|---|
| *G01N 31/00* | (2006.01) | |
| *G01N 33/53* | (2006.01) | |
| *G01N 33/574* | (2006.01) | |
| *G01N 33/50* | (2006.01) | |

(52) U.S. Cl.
CPC ... *G01N 33/57496* (2013.01); *G01N 33/5091* (2013.01); *G01N 33/57415* (2013.01); *G01N 2333/91057* (2013.01); *G01N 2800/52* (2013.01)

(58) Field of Classification Search
None
See application file for complete search history.

(56) References Cited

FOREIGN PATENT DOCUMENTS

| | | |
|---|---|---|
| CA | WO2014067002 | 5/2014 |
| WO | WO2014020444 | 2/2014 |

OTHER PUBLICATIONS

Mackey et al. Breast Cancer Research and Treatment., Feb. 2021, 186(1), 79-87 (Year: 2012).*
Mackey, J., Lai et al.; "N-myristoyltransferase proteins in breast cancer: prognostic relevance and validation as a new drug target", Breast Cancer Res Treat. 2021 Deb; 186(1): 79-87.
Hannaforn B. er al. Expression of microRNA and their gene targets are dysregulated in preinvasive breast cancer: Breast Cancer Res. Mar. 4, 2011;13(2):R24.

* cited by examiner

*Primary Examiner* — Lisa V Cook
(74) *Attorney, Agent, or Firm* — Michael R. Williams; Ryan W. Dupuis; Ade & Company Inc.

(57) ABSTRACT

High levels of nuclear NMT1 are associated with longer relapse free survival in ERα positive breast cancer patients. Both low levels of cytosolic and nuclear NMT1 correlated to very poor clinical outcomes. NMT2 also plays an important function in breast cancer signalling, regulated through phosphorylation. For example, NMT2 phosphorylation status is a key element in the progression of ER+ breast cancer cells. Specifically, nuclear localization of NMT2 is associated with poor outcomes in breast cancer patients.

8 Claims, 12 Drawing Sheets

Death BC

Death BC/Recur

Death BC

Death BC/Recur

PREDICTING PROGNOSIS AND TREATMENT RESPONSE OF BREAST CANCER PATIENTS USING EXPRESSION AND CELLULAR LOCALIZATION OF N-MYRISTOYLTRANSFERASE

PRIOR APPLICATION INFORMATION

The instant application is a 371 of PCT CA 2022/050808, filed May 20, 2022, which claimed the benefit of U.S. Provisional Patent Application 63/190,905, filed May 20, 2021, entitled "PREDICTING PROGNOSIS AND TREATMENT RESPONSE OF BREAST CANCER PATIENTS USING EXPRESSION AND CELLULAR LOCALIZATION OF N-MYRISTOYLTRANSFERASE", the entire contents of which are incorporated herein by reference for all purposes.

BACKGROUND OF THE INVENTION

The human N-myristoyltransferase (NMT) exists in two forms—NMT1 and NMT2. The gene for human NMT1 is located on the long arm of chromosome 17 and the alterative isoforms appear to be splicing variants (Selvakumar P et al., *Prog Lipid Res* 2007, 46(1):1-36) whereas NMT2 is located on chromosome 10. Previous studies have indicated NMT to be solely cytosolic; however, recently, it has been demonstrated that 10-50% may be associated with a particulate fraction (Boutin J A, *Cell Signal* 1997, 9(1):15-35).

The majority of breast cancers arise from epithelial cells lining the ducts of the breast tissue, and are thus categorized as carcinomas (Sharma, G. N., et al., Journal of Advanced Pharmaceutical Technology & Research, 2010. 1(2): p. 109-126). Central to the cell signalling in most breast carcinomas is estrogen signalling. Estrogen signalling is regulated through the interplay between the two distinct estrogen receptor isoforms (ER α and ER β) and their respective splice variants (Heldring, N., et al., Physiol Rev, 2007. 87(3): p. 905-31). Both ERs are members of the nuclear receptor family of transcription factors, dimerizing upon ligand binding and subsequently localizing to the nucleus to initiate gene transcription (Tamrazi, A., et al., Mol Endocrinol, 2002. 16(12): p. 2706-19). ER activated genes are regulated by regions of DNA collectively known as estrogen response elements (EREs) (Klinge, C. M., Nucleic Acids Research, 2001. 29(14): p. 2905-2919). The primary ER ligand, the steroid hormone estrogen, is a potent morphogen responsible for driving the proliferation of epithelial breast tissues following its binding to EREs, as well as a range of other effects in men and women including those on the cardiovascular, musculoskeletal, immune, and central nervous systems (Gustafsson, J. A., Trends Pharmacol Sci, 2003. 24(9): p. 479-85). Specifically, ER mediated translation produces proteins essential in key processes in breast cancer development, including cell division, survival, and angiogenesis (Osborne, C. K., et al., Clin Cancer Res, 2001. 7(12 Suppl): p. 4338s-4342s). ERs may also participate in "nongenomic" signalling through interaction with proteins in other growth signalling pathways (Losel, R. M., et al., Physiol Rev, 2003. 83(3): p. 965-1016).

Of the different biological estrogen forms, 17β-estradiol (E2) is the most potent version and is the form most frequently involved in breast tissue tumorigenesis (Simpson, E. R., J Steroid Biochem Mol Biol, 2003. 86(3-5): p. 225-30). ER α and ER β are known to have some distinct and divergent functions following the E2 response. This is especially evident at the promoters of important proliferation genes, in which ER α and ER β often have opposing effects (Liu, M. M., et al., J Biol Chem, 2002. 277(27): p. 24353-60). Of the two ER isoforms, ER α overexpression is associated with breast cancer: over half of primary breast cancers exhibit ER α overexpression and approximately 70% of these are sensitive to anti-estrogen therapy (Ali, S. and R. C. Coombes, J Mammary Gland Biol Neoplasia, 2000. 5(3): p. 271-81). Typically, these ER positive breast cancers are treated with either selective estrogen receptor modulators (SERMs), such as tamoxifen, or they are treated with aromatase inhibitors, including anastrozole, exemestane and letrozole (AIs). SERMs generally bind to the ER and act as a competitive inhibitor to block estrogen growth signalling; however, tamoxifen (and other triphenylethylene drugs) does behave as a partial agonist, displaying tissue-selective pharmacology. In fact, evidence suggests that tamoxifen activates the ER, with the subsequent conformational changes of tamoxifen-bound ER resulting in the preferential recruitment of corepressor complexes that lead to gene silencing. Currently, tamoxifen remains the gold standard treatment for primary breast tumors. Due to some of the anti-proliferation effects of ER β signalling, ER β agonists have also been considered in the treatment of some breast cancers (Montanaro, D., et al., J Mol Endocrinol, 2005. 35(2): p. 245-56). The aforementioned treatments are examples of endocrine therapy (also known as hormonal therapy).

ER+ Positive Breast Cancer

Hormone receptor positive breast cancer cells overexpress ER and/or PR, are dependent on the production of endogenous estrogen or progesterone to activate hormone dependent signalling pathways which regulate cellular proliferation rates. The ER has both nuclear (genomic) and non-nuclear (non-genomic) functions and is the major driver of the majority of breast cancers. ER+ breast cancers account for approximately 75% of all diagnosed breast cancer cases (C. K. Osborne and R. Schiff, *Annu Rev Med*, vol. 62, pp. 233-247, 2011). As discussed above, ER exist in two isoforms, ERα and ERβ, which belong to the steroid hormone receptor family of nuclear receptors. ERα is the receptor found to be overexpressed in ER+ breast cancer cells and therefore serves as a primary biomarker for ER+ breast cancer prognosis (M. H. Zhang et al., *Biomed Rep*, vol. 2, no. 1, pp. 41-52, January 2014).

Selective Endocrine Receptor Modulators (SERMs)

As discussed above, there are primarily three classes of agents used to treat ER+ breast tumors: Selective endocrine receptor modulators (SERMs, such as tamoxifen), estrogen synthesis inhibitors (aromatase inhibitors (AIs), such as anastrozole) and selective endocrine receptor down regulators (SERDs, such as fulvestrant) (M. Giuliano et al., The Breast, vol. 20, pp. S42-S49, October 2011). Breast cancer tumors are typically removed by surgery and/or treated with chemotherapy, radiation, and various adjuvant drug therapies such as SERMs. Tamoxifen, which acts as an ER antagonist, competitively inhibiting endogenous estrogen molecules from binding to the ER active site, is considered to be one of the most effective forms of hormonal therapy and is the most commonly prescribed SERM for ER+ breast cancer patients.

Despite the relative success of endocrine therapies in treating breast cancer, de novo and developed resistance to these therapies (endocrine resistance) are still issues of major concern. Almost 50% of breast cancer patients with primary tumors exhibit de novo resistance to first line tamoxifen treatments, with tamoxifen sensitive individuals often acquiring resistance to the drug after an initial positive response. Actual ER expression loss accounts for only a small fraction (10%) of endocrine resistance cases in primary and metastatic tumors (Sighoko, D., et al., Oncologist, 2014. 19(6): p. 592-601). Aberrant PI3K/AKT/mTOR signalling occurs in about 70% of breast cancers, with signalling molecules downstream of the IGF1R receptor also contributing to endocrine resistance, including mutations to the PIK3CA, AKT1, AKT2, PDK1, PTEN and INPP4B genes (Fu, X. et al., Breast, 2013. 22 Suppl 2: p. S12-8).

The PI3K/AKT/mTOR signalling pathway is involved in regulating glucose metabolism, angiogenesis, cell survival, proliferation, and migration, and is often dysregulated in many types of cancer, including breast cancer. The PI3K pathway is triggered by insulin, and growth factors such as EGF, FGF and IGF-1. AKT, which is central to the PI3K pathway, is a serine/threonine protein kinase and proto-oncoprotein (Bellacosa, A., et al., Adv Cancer Res, 2005. 94: p. 29-86). AKT is normally cytoplasmic, but locates to the inner cell membrane by AKT's Plekstrin Homology (PH) domain binding to PIP3, exposing activation sites on AKT for hydroxyl group phosphorylation. Primary phosphorylation of AKT sites for activation are at T308, phosphorylated by phospho-inositide dependent kinase 1 (PDK1), and S473, which is phosphorylated by mTOR complex2 (mTORC2). In ER+ breast cancer cell lines, upon phosphorylation at both T308 and S473, AKT is fully activated and translocates to the cytoplasm, nucleus or other sub-cellular compartments, where it phosphorylates other substrates. A downstream target of AKT is mTOR, which is a kinase that regulates the cellular processes of cell growth, proliferation in response to nutrient/energy availability, signalling stimuli and translation of protein. it has been demonstrated that AKT overexpression leads to decreased NMT activity (Shrivastav, A., et al., J Pathol, 2009. 218(3): p. 391-8). Preliminary studies in our lab have demonstrated that mTOR interacts with and potentially phosphorylates NMT1.

NMT Subcellular Localization

Despite the overlapping targets of NMT1 and NMT2 and their variants, they appear to have different roles in cell apoptosis, during which the myristoylated proteome undergoes drastic changes (Perinpanayagam, M. A., et al., Faseb j, 2013. 27(2): p. 811-2). Ablation of NMT2 has been shown to induce a 2.5× greater rate of apoptosis over NMT1 knockdown in SK-OV-3 ovarian carcinoma cells (Ducker, C. E., et al. Mol Cancer Res, 2005. 3(8): p. 463-76).

Depletion of NMT2 also yielded a shift in BCL family proteins towards a state of apoptosis. These findings support the notion that NMT1 may be the primary NMT involved in driving apoptosis, with NMT2 associating with suites of pro-growth signalling proteins. The same study found that dual depletion of NMT1 and 2 was lethal and that this effect was p53 independent. The line of division between these enzymes' roles may be drawn through their dynamic and differential localization during apoptosis, among other cell states. Perinpanayagam et al demonstrated that both NMT isoforms are cleaved by caspases during apoptosis, in which NMT1 and NMT2 localization changes significantly ((Perinpanayagam, M. A., et al. Faseb j, 2013. 27(2): p. 811-2). NMT1 was shown to be cleaved at Aspartic Acid-72 by either effector caspase 3 or extrinsic caspase 8; NMT2 was shown to be cleaved at Aspartic Acid-25 by effector caspase 3. Caspase-3 is an executioner caspase, which catalyzes the cleavage of many cellular proteins involved in programmed cell death (Nicholson, D. W., Cell Death Differ, 1999. 6(11): p. 1028-42). Following caspase cleavage, which leaves behind a poly-basic domain stretch, a greater population of NMT1 translocated to cytoplasm (55%) from membrane bound whereas NMT2 underwent an even greater shift in localization following caspase cleavage which removed a negatively charged domain, rendering 80% of NMT2 membrane bound as opposed to 62% cytoplasmic prior to caspase cleavage.

Interestingly, serine residues (which are capable of being phosphorylated) within the human NMT isoforms appear to be homologous between different species and between the isoforms themselves. Specifically, serine 47 of NMT1 is similar in relative position to serine 38 of NMT2, with respect to the poly-lysine region in the N-terminus. Additionally, serine 68 which follows the poly-lysine domain of NMT2 is similar in position with serine 73 of NMT1, which has also been identified as phosphorylated in NMT1 following an ultra-deep human phosphoproteome analysis using a human cancer cell line (Sharma, K., et al., Cell Rep, 2014. 8(5): p. 1583-94). The conservation of phosphorylated serines on either side of the poly-lysine region of the NMTs suggests that these residues may play an important role in the regulation of NMT localization within the cell.

SUMMARY OF THE INVENTION

According to a first aspect of the invention, there is provided a method of determining prognosis of a hormone positive breast cancer patient comprising:
  extracting a cell sample from a breast tumor of a hormone positive breast cancer patient; and
  determining nuclear and cytoplasmic levels of NMT1 in one or more cells of the cell sample;
  wherein: if cytoplasmic levels of NMT1 are high, the prognosis is poor;
  if nuclear levels of NMT1 are high, the prognosis is good; and
  if both nuclear and cytoplasmic levels are low, the prognosis is worse than poor.

According to another aspect of the invention, there is provided a method of determining the prognosis of a breast cancer patient comprising:
  extracting a cell sample from a breast tumor of a patient;
  determining the cellular localization of NMT2 in at least one cell of the cell sample;
  wherein if the at least one cell of the cell sample is positive for nuclear NMT2, the prognosis is poor, and
  if the at least one cell of the cell sample is negative for nuclear NMT2, the prognosis is good.

According to another aspect of the invention, there is provided a method of determining the prognosis of a triple-negative breast cancer patient comprising:
  extracting a cell sample from a breast tumor of a patient;
  determining the cellular localization of NMT2 in at least one cell of the cell sample;
  wherein if the at least one cell of the cell sample shows positive nuclear localization of NMT2, the prognosis is poor.

According to another aspect of the invention, there is provided a method of slowing progression or improving outcome of a breast cancer tumor comprising:
  administering an effective amount of an NMT2 serine phosphorylation inhibitor to a patient having a cancerous breast tumor, thereby preventing phosphorylation of NMT2 and subsequent nuclear localization of NMT2.

According to another aspect of the invention, there is provided a method of identifying a compound capable of inhibiting nuclear translocation of cytoplasmic NMT2 comprising:

in an in vitro system, growing a plurality of test cells under conditions suitable for nuclear translocation of cytoplasmic NMT2 in the presence of a compound of interest wherein but for the presence of the compound of interest, cytoplasmic NMT2 will migrate into the nucleus of a respective one cell of the plurality of cells; and determining if cytoplasmic NMT2 has translocated into the nucleus of at least one of the plurality of test cells in the presence of the compound of interest, wherein if less cytoplasmic NMT2 has translocated into the nucleus of the at least one representative cell of the plurality of cells than translocated into the nucleus of at least one control cell grown under similar conditions except for the presence of the compound of interest, the compound of interest inhibits nuclear translocation of cytoplasmic NMT2.

DESCRIPTION OF THE PREFERRED EMBODIMENTS

Figure 1:
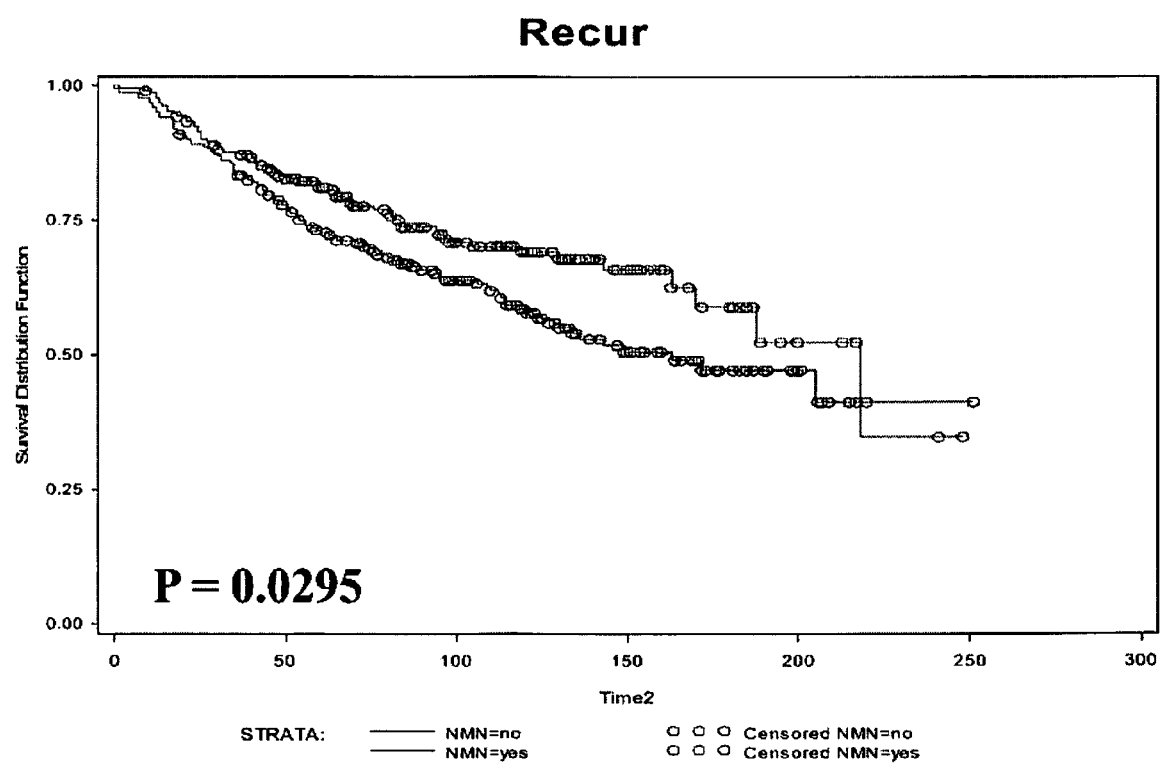
FIG. 1. High NMT1 nuclear levels correlate to longer reoccurrence free survival. Patients were separated into low or high categories based on the median H-score. Kaplan Meier curves were generated to assess whether any parameters associated with a significant change in patient survival. Reoccurrence analysis of low or high nuclear NMT1 levels.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As discussed herein, high levels of nuclear NMT1 are associated with longer relapse free survival in ERα positive breast cancer patients, subsequently treated with tamoxifen, in univariate analysis. Interestingly, both low levels of cytosolic and nuclear NMT1 correlated to very poor clinical outcomes, as discussed herein.

Specifically, nuclear localization of NMT1, accompanied by low cytoplasmic expression of NMT1, was associated with relapse free recovery following endocrine therapy. The opposite NMT1 localization pattern, high cytoplasmic expression of NMT1, was associated with endocrine therapy resistance and bad prognosis. Thus, we hypothesized that NMT1 is phosphorylated downstream of the PI3K/AKT/mTOR/ER signalling axis by mTOR, and that this phosphorylation event is implicated in NMT1's localization to the nucleus and in good ER+ breast cancer treatment outcome following endocrine therapy. Furthermore, we predicted that the NMT2 isozyme may also be playing an important function in breast cancer signalling, and that this role may also be regulated through phosphorylation.

Furthermore, this study identified and explored potential mTOR or AKT mediated phospho-sites on the NMT1 protein, as well as identified putative phospho-sites on the NMT2 isozyme for future analysis. Datamining using Kinexus Phosphonet and PhosphositePlus revealed that S40 and S47 (NMT1), and S38 and 68 (NMT2) are prime candidates for phosphorylation by mTOR.

Notably, a putative poly-lysine based nuclear localization sequence (NLS) was identified during this study within the N-termini of NMT1 and NMT2. The putative NLS in both proteins is located nearby the residues predicated to be phosphorylated by mTOR. Phosphorylation of NMT may be a possible mechanism in which NMT containing a poly-lysine region is primed for or inhibited from nuclear or ER localization. The presence of S47 phosphorylated NMT1 in the nucleus suggests that this phosphorylation event may be required for nuclear localization of NMT1; the presence of S47 phosphorylated NMT1 following DNA damage suggests that nuclear phopsho-NMT1 may be involved in swinging gene transcription towards apoptosis.

Additionally, serine 38 and serines 66, 68 and 70 nearby the poly-lysine region of NMT2 have been shown to be phosphorylated in cancerous tissues (Stuart, S. A., et al., A, Mol Cell Proteomics, 2015. 14(6): p. 1599-615; Zanivan, S., et al., J Proteome Res, 2008. 7(12): p. 5314-26).

It is apparent that most predicted and/or observed phosphorylation events on the NMT isozymes are concentrated around the putative NLS within the N-terminus, regardless of whether they are predicted to be mediated by mTOR. Phosphorylation adjacent to an NLS is a well-known mechanism to regulate importin a mediated translocation of a protein to the inside of the nucleus (Harreman, M. T., et al., J Biol Chem, 2004. 279(20): p. 20613-21). It is plausible that the predicted phosphorylation events may stabilize the structure of the nearby NLS and keep it exposed, as the N-termini of both NMT1 and NMT2 are normally highly disordered.

The S47 residue proved to be a good candidate to study the structural stabilization of the NLS following phosphorylation. Furthermore, phospho-sites tend to be present in the disordered regions of proteins, a pattern that is apparent in NMT1 and NMT2, suggesting that the disordered N-terminal region of NMTs is the primary regulatory region of the enzyme (Landry, C. R., E. D. Levy, and S. W. Michnick, Trends Genet, 2009. 25(5): p. 193-7). This disordered N-terminal region is exposed and highly flexible, making it an easy target for potentially stabilizing phosphorylation. Indeed, the multi-phosphorylation model of NMT1 in which the putative phospho-sites surrounding the NLS were phosphorylated, predicted that the N-terminus of the protein stabilized to form an exposed structure resembling a Helix-Turn-Helix motif. This type of motif is associated with DNA binding and is common to many transcription factors.

MCF7 breast cancer cell lines were established that express various mutant versions of NMT1 fused to a GFP tag. These include variants with either null mutations to the potential phospho-sites (S40A, S47A, and S256A) or phosphorylation mimicking mutations to the sites (S40E. S47E, S256E). We hypothesized that phosphorylation of these sites was involved in shuttling NMT1 to the nucleus or endoplasmic membrane system. Thus, we expected that mutating these sites to alanine phospho-knockouts would result in an NMT1-GFP fusion protein that remained primarily in the cytoplasm. Overall, our prediction was observed, with S40A, S47A and S256A expressing the fusion protein diffusely through the cytoplasm. Inversely, we predicted that at least one of the glutamic acid mutations would result in at least one cell line that exclusively expressed NMT1 in the nucleus; however, results were mixed. Localization that appeared to overlap with the nucleus was observed to a certain degree in S40, S47, and S256 phosphomimics; however, many cells in these populations expressed cytoplasmic NMT1. Unlike the wildtype NMT1-GFP or the alanine mutants, which expressed fusion protein evenly throughout the cytoplasm, S40E and S256E cells that expressed cytoplasmic fusion protein did so in localized areas. These areas often constituted a patch of expression adjacent to the nuclear region, indicating potential localization to the ER. Overall, these findings suggest that phosphorylation of all three sites may be somehow involved in translocation of NMT1 to the nucleus or nuclear membrane, with phosphorylation of S40 and/or S256 involved in translocation of NMT1 to the ER. Within the nucleus, it is possible that NMT1 is playing a role in transcriptional regulation.

The observation of nuclear NMT1, coupled with the identification of a putative DNA interacting NLS, sparked our interest in exploring NMT1's role in the nucleus. We predicted that NMT1 might be interacting with a myristoylated transcriptional co-repressor, BASP1. Immunoprecipitation of BASP1 co-immunoprecipitated NMT1 protein.

Confirmation of the BASP1-NMT1 interaction within the nucleus of MCF7 breast cancer cells led us to investigate a potential interaction of NMT1 with DNA. We showed for the first time through ChIP analysis that NMT1 appears to interact with the P21 and IGF1R growth genes, repression targets of BASP1. Both P21 and IGF1R expression are driving factors in the progression of many cancers, including breast cancer. It is possible that the association of nuclear NMT1 with good breast cancer prognosis is due in part to repression of these and other growth genes.

Although NMT1 and NMT2 are not redundant in function, they share 77% amino acid sequence homology with analogous putatively phosphorylated serine residues.

As discussed herein, NMT2 phosphorylation status is a key element in the progression of ER+ breast cancer cells.

As used herein, "prognosis" refers to for example a "best estimate" of how a cancer will affect a patient, that is, the likely outcome of the cancer. As will be appreciated by those of skill in the art, there are many methods for assigning a prognostic score for a particular patient, that relies on many factors. Accordingly, as used herein, "determining prognosis" refers to the fact that the levels and/or subcellular location of NMT1 and/or NMT2 may represent one prognostic factor in an overall prognosis determination. As such, referring to the prognosis as being "good" or "favorable" indicates that the observed levels and/or subcellular location of NMT1 and/or NMT2 contribute positively to a prognostic score whereas referring to the prognosis as "poor" indicates that a negative contribution is being made to the prognostic score and referring to the prognosis as "worse" indicates that a more negative contribution is being made to the prognostic score. That is, a "worse" prognosis means that the prognostic score is reduced whereas prognosis as "good" or "favorable" means that the prognosis score is increased.

According to an aspect of the invention, there is provided a method of determining prognosis of a hormone positive breast cancer patient comprising:

extracting a cell sample from a breast tumor of a hormone positive breast cancer patient; and determining nuclear and cytoplasmic levels of NMT1 in one or more cells of the cell sample;

wherein: if cytoplasmic levels of NMT1 are high, the prognosis is poor or lowered or a prognostic score is lowered or decreased or reduced;

if nuclear levels of NMT1 are high, the prognosis is good or improved or a prognostic score is increased or improved; and if both nuclear and cytoplasmic levels are low, the prognosis is worse or the prognostic score is lowered or decreased more than for a poor prognosis.

As discussed herein, cytoplasmic levels and nuclear levels of NMT1 can be determined by a variety of means known in the art. For example, in some embodiments, microscopic analysis of at least one cell from the cell sample may be carried out. In these embodiments, the position of NMT1 may be localized, for example, by antibody binding and subsequent immunofluorescence and/or immunohistochemistry. In this manner, overall levels of NMT1 as well as the cellular localization thereof can be determined. Furthermore, one of skill in the art can easily determine if overall levels of NMT1 are high in either the cytoplasm or nucleus of a given cell for example by comparison with or simply based on knowledge of a control. For example, such a control may be a "positive" control from one or more cells known to have high cytoplasmic or nuclear levels of NMT1 or a "negative" control from one or more cells known to have low cytoplasmic or nuclear levels of NMT1.

As will be known by those of skill in the art, one method for carrying out such a determination is called an H or IHC Score. In methods such as this, slides are scored using standard light microscopy. For example, IHC scores are derived from assessment of both average staining intensity across the two tumor cores (scale 0 to 3) and percentage of positive cells (0 to 100%). These two scores, when multiplied, generate an IHC or H-score of 0 to 300. An "H" score higher than 100 is considered high and less than 100 is considered low for nuclear NMT1, whereas, an "H" score higher than 150 is considered high and lower than 150 is considered low for cytoplasmic NMT1.

In some embodiments, if cytoplasmic levels of NMT1 are determined to be high, for example, having an H score or IHC score of greater than 150, as discussed above, this indicates that the response of the patient to endocrine therapy will be poor, meaning that the patient is at risk for cancer recurrence and death due to breast cancer. Furthermore, a patient with this prognosis would be given a systemic cancer treatment, such as for example chemotherapy, and monitored more frequently for possible recurrence, that is, would be scheduled for more frequent doctor visits and/or examinations than would a patient with a "good" or "favorable" prognosis as understood and accepted by those of skill in the art.

In some embodiments, if nuclear levels of NMT1 are determined to be high, that is, for example, an H score of greater than 100, as discussed above, this indicates that the endocrine therapy response of the patient is likely to be good, and that the patient is at significantly lower risk of recurrence and death due to breast cancer. Accordingly, a patient with this outcome can be administered endocrine therapy and monitored less frequently for possible recurrence.

If both nuclear and cytoplasmic NMT1 levels are low (for example, an H score less than 100 or less than 150 respectively), the endocrine therapy response is worse, with significantly higher risk or rate of recurrence and death due to breast cancer. A patient with this outcome should be assigned a more aggressive systemic therapy than endocrine therapy and monitored much more frequently, as discussed above.

According to another aspect of the invention, there is provided a method of determining the prognosis of a breast cancer patient comprising:

extracting a cell sample from a breast tumor of a patient;

determining the cellular localization of NMT2 in at least one cell of the cell sample;

wherein if the at least one cell of the cell sample is positive for nuclear NMT2, the prognosis is poor, and if the at least one cell of the cell sample is negative for nuclear NMT2, the prognosis is good.

For example, a poor prognosis means that the patient is at risk of recurrence or death due to breast cancer within the first ten years of diagnosis and should be given systemic treatment (chemotherapy) and monitored for recurrence more frequently, as discussed herein.

For a patient with a good prognosis, wherein there is no nuclear NMT2, the patient may be put on endocrine therapy (in the case of hormone-positive cancers) alone for the first ten years and then just monitored for the next ten years.

According to another aspect of the invention, there is provided a method of determining the prognosis of a triple-negative breast cancer patient comprising:

extracting a cell sample from a breast tumor of a patient;

determining the cellular localization of NMT2 in at least one cell of the cell sample;

wherein if the at least one cell of the cell sample shows positive nuclear localization of NMT2, the prognosis is poor.

If the prognosis is poor, most of the breast cancer patients will die within the first ten years after diagnosis, usually within the first 4 years of diagnosis. These patients should be placed on increased surveillance.

As will be appreciated by one of skill in the art, if there is no nuclear localization of NMT2, the prognosis is better or favorable, as discussed herein. Endocrine therapy will be the adjuvant therapy to all hormone receptor breast cancer irrespective of the NMT2 status. Positive nuclear NMT2 staining will be suggestive of the poor prognosis and recurrence wherein additional combination therapy along with endocrine therapy may benefit the patient.

As discussed herein, after ten years, the nuclear NMT2 doesn't matter much but high cytoplasmic NMT2 still relates to a bad outcome. Specifically, the survival outcome is poor for very high NMT2 in the cytoplasm. This remains true as an intermediate predictor for high NMT2 in the cytoplasm is a poor predictor.

As will be appreciated by one of skill in the art, while in some embodiments, at least one cell of the cell sample is examined, it is preferable that a statistically significant number of cells are analyzed and the results analyzed, for example, averaged. In some embodiments, at least about one hundred cells from the cell sample are examined for determining NMT1 and/or NMT2 levels and/or cellular location or subcellular location as discussed herein.

According to another aspect of the invention, there is provided a method of slowing progression of a breast cancer tumor or improving outcome of a breast cancer treatment comprising:

administering an effective amount of an NMT inhibitor to a patient having a cancerous breast tumor, thereby preventing phosphorylation of NMT2 and subsequent nuclear localization of NMT2.

In some embodiments, the NMT inhibitor is a compound that inhibits both NMT1 and NMT2 activity.

In some embodiments, the NMT inhibitor is an NMT2 inhibitor, that is, specific for inhibition of NMT2 activity.

In some embodiments, the NMT2 inhibitor is an NMT2 serine phosphorylation inhibitor.

In some embodiments, the NMT2 serine residue at which phosphorylation is being inhibited is S38 or S68.

In some embodiments of the invention, the serine phosphorylation inhibitor blocks access to S38 or S68 for the kinase, for example, by binding to a region of NMT2 encompassing S38 or S68 as discussed herein and/or by disrupting the NMT2 nuclear localization signal (NLS).

In some embodiments of the invention, the NMT2 serine phosphorylation inhibitor is an antibody or a small molecule, as discussed herein.

As will be appreciated by one of skill in the art, since the intervention is at the N-terminus, the enzymatic activity of NMT2 is not inhibited as the catalytic domain is in the C-terminus According to another aspect of the invention, there is provided a method of identifying a compound capable of inhibiting nuclear translocation of cytoplasmic NMT2 comprising:

in an in vitro system, growing a plurality of test cells under conditions suitable for nuclear translocation of cytoplasmic NMT2 in the presence of a compound of interest wherein but for the presence of the compound of interest, cytoplasmic NMT2 will migrate into the nucleus of a respective one cell of the plurality of cells; and determining if cytoplasmic NMT2 has translocated into the nucleus of at least one of the plurality of test cells in the presence of the compound of interest, wherein if less cytoplasmic NMT2 has translocated into the nucleus of the at least one representative cell of the plurality of cells than translocated into the nucleus of at least one control cell grown under similar conditions except for the presence of the compound of interest, the compound of interest inhibits nuclear translocation of cytoplasmic NMT2.

As will be appreciated by one of skill in the art, any suitable cells could be used in such a method and these cells could be grown under any suitable growth conditions, for example, under standard cell culture growth conditions.

In some embodiments of the invention, nuclear translocation of NMT2 is determined by measuring proliferation of the test cells, as cells that have NMT2 in the nucleus become highly proliferative. As is known by those of skill in the art, there are a large number of methods for monitoring and/or measuring cell proliferation, that is, cell growth, known in the art which can be used within this aspect of the invention.

The invention will now be further explained and/or elucidated by way of examples; however, the invention is not necessarily limited to or by the examples.

Results obtained from PhosphoNet and PhosphoSitePlus databases revealed that the most likely site of phosphorylation of NMT2 by mTOR is serine 38 followed by serine 68. NLStradmus query results that the poly lysine sequence, which runs from position 46 to 59 in the NMT2 primary structure, is likely acting as an NLS. Such a NLS would allow NMT2 protein to couple to importin, a shuttling protein which allows for the passage of protein across the cell's nuclear membrane. A Multiple sequence alignment performed by Maga 7.0 software affirms that both of the S38 and S68 phosphorylation sites and the NLS are highly conserved in the NMT2 amino acid sequence across various species including humans. This high level of conservation signifies the importance of these sites in the regulation and/or function of NMT2. The sequence alignment also revealed a highly conserved poly lysine sequence from residues 46 to 59 which is flanked by the S38 and S68. This suggest that phosphorylation of these serine residues could lead to conformational change of the NLS of NMT2 which may function to determine the interactions of NMT2 with nuclear pore shuttling proteins such as importin. It is plausible that phosphorylation of site 38 or 68, or of both sites simultaneously, may be regulating whether the NLS of NMT2 is exposed on the surface or embedded within the protein. If the NLS is exposed this would make it possible for importin, a nuclear pore shuttling protein, to interact with NMT2 and escort it over the nuclear membrane and into the nucleus.

Example 1—Expression of NMT2-GFP in MCF7 Cells

All NMT2 plasmid constructs were successfully transfected into MCF7 cells. Transfected cells for MCF7-GFP-NMT2, MCF7-GFP-NMT2-S38A, MCF7-GFP-NMT2-S38E, MCF7-GFP-NMT2-S68A, MCF7-GFP-NMT2-S68E and MCF7-GFP-NMT2-K49E lines displayed the expression of GFP under fluorescent microscopy. The results obtained from fluorescent microscopy analysis of these cell cultures excluded the S68A, S68E and K49E cell lines from further research. To further confirm the presence of NMT2 GFP fusion protein in the three remaining transfected cell lines, whole cell lysates were collected from each line, along with the MCF7 line, and analyzed by Western blot. The analysis displayed the expression of polypeptide band at the 60 kDa region of the membrane for all four lines. The 60 kDa region corresponds with the molecular weight of endogenous NMT2 protein. The analysis also displayed polypeptide bands at the 87 KDa region of the membrane in all three NMT2 GFP transfected cell lines. This region corresponds with the molecular weight of NMT2-GFP and confirmed the presence of NMT2 GFP in the three transfected lines.

Example 2—Sub Cellular Expression Patterns of NMT2 GFP

To determine if NMT2 phosphorylation status at serine 38 and 68 residues regulates its subcellular localization, NMT2-GFP fusion protein serine 38 or 68 residues were changed to either alanine residues (phospho-dead) or glutamic acid residues (phospho-mimic). A lysine residue at position 49 in the NMT2 putative NLS was also changed to a glutamic acid residue to determine if disruption of the NLS would affect NMT2 localization. All forms of the NMT2 GFP fusion protein, including non-mutated NMT2 GFP, were expressed in MCF7 ER+ breast cancer cells.

Disruption of the NMT2 NLS did appear to result in no nuclear localization of the NMT2 K49E GFP as expected.

As for the serine 38 mutations, when the residue was mutated to an alanine, NMT2-GFP showed no nuclear localization. However, when the residue was mutated to a glutamic acid, nuclear localization of the NMT2-GFP was greatly increased. Many S38E cells show very prominent expression of the NMT2 GFP inside their nuclei. Results from fluorescent microscopy of MCF7-GFP-NMT2-S38A or MCF7-GFP-NMT2-S38E stained for—DAPI show direct overlap of the expression of the NMT2 S38E GFP and the nuclei staining DAPI stain. Results from a Western blot analysis of nuclear fractions for the MCF7-GFP-NMT2, S38A and S38E cell lines show strong expression of NMT2-GFP in the nuclear fractions of the S38E line and very little to no expression in the nuclear fractions of the S38A line. These results together confirmed the presence of nuclear NMT2 GFP in the S38E line.

It appears that phosphorylation status at serine 38 regulates the subcellular localization patterns of NMT2.

Example 3—Nuclear NMT2 Increases MCF7 Proliferation Rates

To determine if the constitutive phosphorylation of NMT2 protein plays any role in MCF7 cellular proliferation rates, two cellular proliferation assays were performed. In the trypan blue assay, by the 72 hour time point, the S38E cell line had grown from 12,500 cells/ml of media (50,000 cells total) to approximately 1.1 million cells/ml while the MCF7 and the MCF7-GFP-NMT2 control lines had only grown to approximately 600,000 cells/ml and the S38A line had only managed to grow to approximately 400,000 cells/ml. The S38E line proliferated at nearly twice the rate of the control lines and more than twice the rate of the S38A line. A t-test statistical analysis found a significant difference between the growth rates of the MCF7 and S38E and cell lines with a P-value of 0.002 at the 72-hour time point (double asterisks in FIG. 5) and a P-value of 0.05 at the 96-hour time point (single asterisk). This significance likely decreased (from 0.002 to 0.05) as time elapsed from 72 to 96 hours due to lack of space in the S38E wells causing cells to die and approach MCF7 cell counts. A significant difference was also found between the proliferation rates of the S38A and MCF7 cell lines at the 96-hour time point (double asterisks) with a P-value of 0.02. Also, to be noted, the S38E cell line was the first line to obtain enough cellular mass to reach the point of massive cellular death due to a lack of floor space in the culture plate and a lack of nutrient in the media, confirming that the S38E line grew and proliferated the quickest.

Figure 6:
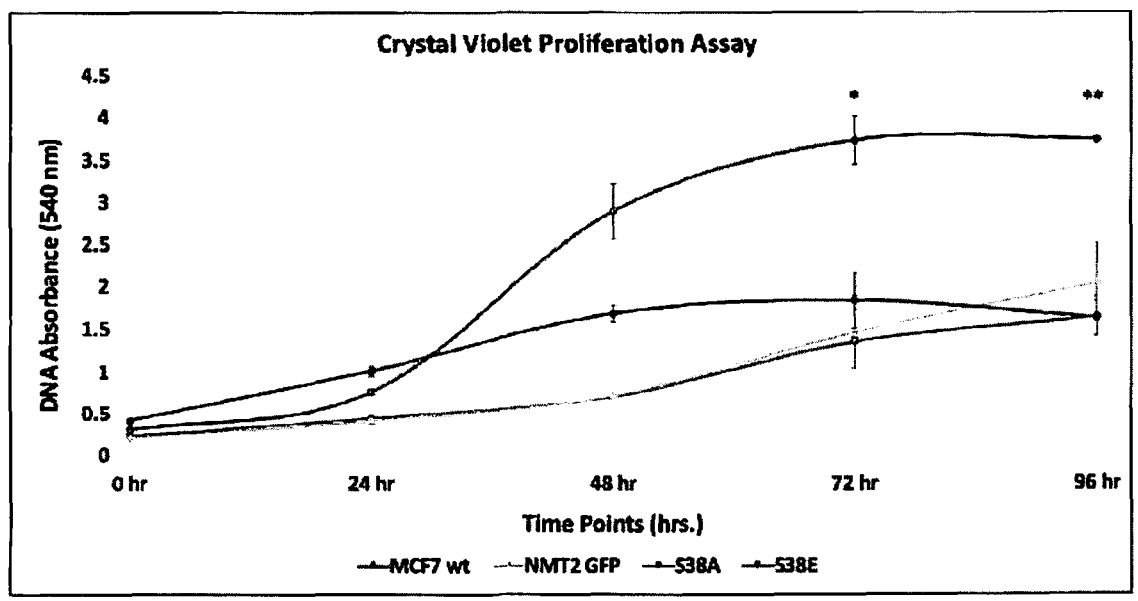
FIG. 6: Crystal violet assay for cellular proliferation rates of MCF7 wt and MCF7 cells expressing phospho-site mutated NMT2 proteins. Each point is an average of three readings and error bars represent+standard deviation. The single asterisk (*) represents a t-test P-value significance factor of <0.05 in proliferation rates between the MCF7 and MCF7-GFP-NMT2-S38E cell lines. The double asterisks (**) represents a t-test P-value significance factor of <0.01 in proliferation rates between the MCF7 and MCF7-GFP-NMT2-S38E cell lines.
Figure 7:
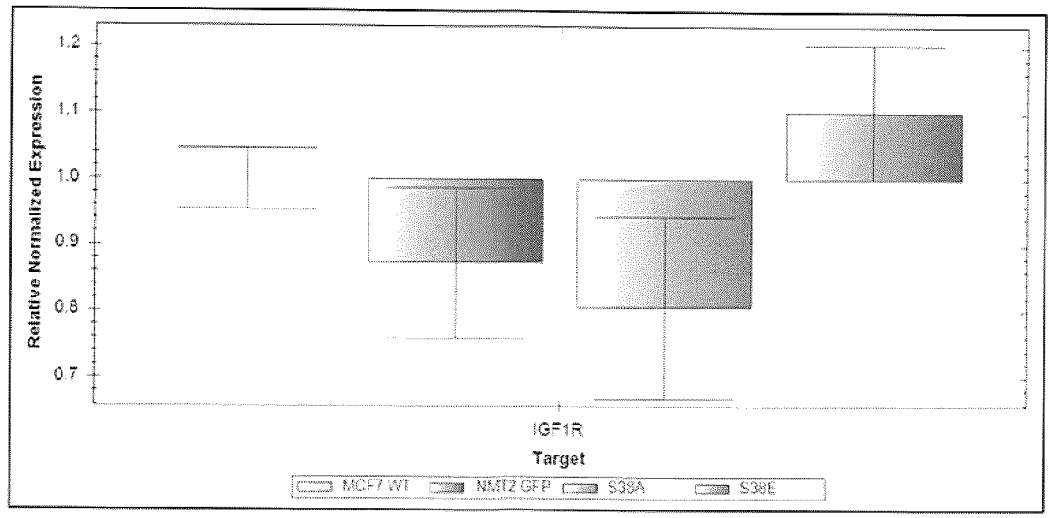
FIG. 7. Expression levels of IGF1R mRNA in the four cell lines of interest.

Results for the crystal violet assay followed a similar tread. Again, at the 72- and 96-hour time points, the S38E line was proliferating significantly faster than the two control lines. The S38A line also appeared to be proliferating more slowly than the two control lines. A t-test statistical analysis revealed a significant difference between the proliferation rate of the MCF7 and S38E cell lines at the 72- and 96-hour time points with P-values of 0.05 (single asterisk in FIG. 6) and 0.003 (double asterisk in FIG. 6) respectively. The significance increased (from 0.05 to 0.003) as time elapsed from 72 to 96 hours due to the faster growth rate of the S38E cell line. Based on the results of these proliferation assays, it appears that preventing NMT2 phosphorylation at site 38 slows the proliferation rate of MCF7 cells while constitutive phosphorylation of this site increases the rate. It is plausible that NMT2, which has accessed the nucleus of the cell, may play a role in transcription regulation and thus may be contributing to the regulation of proliferation.

Example 4—NMT2 Phosphorylation Status and the IGF (PI3K/Akt/mTOR) Pathway

One of the key regulating proteins of the insulin like pathway is the transmembrane IGF1R protein. Activation of IGF1R leads to activation of all downstream proteins of the pathway. Therefore, increased expression of IGF1R could lead to increased activity in this pathway which in turn could lead to increased cellular proliferation rates.

Figure 5:
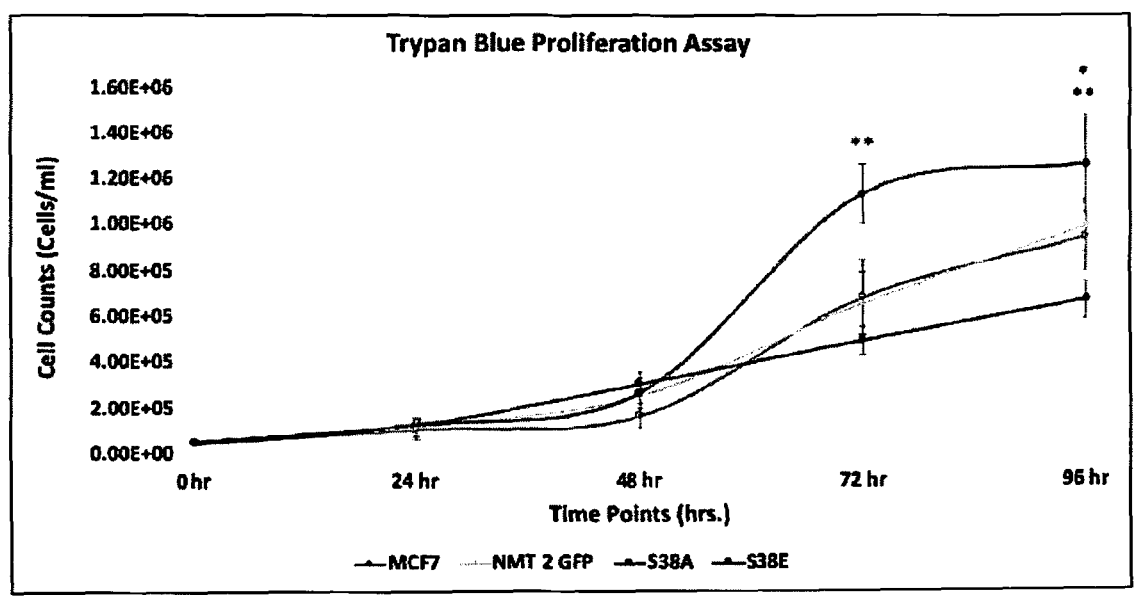
FIG. 5. Trypan blue assay of cellular proliferation rates of MCF7 and MCF7 cells expressing phospho-site mutated NMT2 proteins. Each point is an average of three experiments and error bars represent+standard deviation. The double asterisks (**) represents a t-test P-value significance factor of <0.01 in proliferation rates between the MCF7 and MCF7-GFP-NMT2-S38E cell lines. The single asterisk (*) represents a t-test P-value significance factor of <0.05 in proliferation rates between the MCF7 and MCF7-GFP-NMT2-S38E cell lines. The double asterisks (**) represents a t-test P-value significance factor of <0.01 in proliferation rates between the MCF7 and MCF7-GFP-NMT2-S38A cell lines.

Increased expression and/or hyperactivation of IGF1R is one of the hallmark features of breast cancers and is being pursued as a therapeutic target. Therefore, RT-qPCR was performed to determine the relative expression rates of the IGF1R transcript in MCF7, MCF7-GFP-NMT2, MCF7-GFP-NMT2-S38A and MCF7-GFP-NMT2-S38E cell lines (FIG. 5). Relative to MCF7 cells, the results show increased expression of IGF1R transcript in the S38E line and an under expression of the transcript in the S38A line. The transcription rates of IGF1R gene appear to be greater in the MCF7 cells which are expressing constitutively phosphorylated, at serine 38, NMT2 protein. The MCF7 cells which are expressing NMT2 which cannot be phosphorylated at serine 38 are showing lower transcription rates.

Example 5—NMT2 Localization Status and MCF7 Metastasis

MCF7 cells are normally considered to be weakly metastatic (R. B. Hazan et al., *The Journal of Cell Biology*, vol. 148, no. 4, pp. 779-790, February 2000).

Investigation into the expression patterns of tight junction related claudin family proteins was initiated for the MCF7, MCF7-GFP-NMT2, MCF7-GFP-NMT2-S38A and MCF7-GFP-NMT2-S38E cell lines. Protein expression levels for five members of the claudin family, claudin 1-5, were analyzed by Western blot. No distinctive patterns of expression were observed for any of the claudins except for claudin 1. A previous study suggested that decreased expression of claudin 1 protein may play a role in breast cancer invasion and metastasis and that low claudin 1 expression closely correlates with recurrence status in breast cancer (S. Morohashi et al., *International Journal of Molecular Medicine*, vol. 20, no. 2, pp. 139-143, August 2007). Western blot analysis of claudin 1 protein revealed an increase in expression of the protein in the S38A line relative to MCF7 cells. A t-test statistical analysis of the western blot data showed a significant difference (P-value=0.018) in claudin 1 protein expression between the S38A and S38E lines. This indicates that when NMT2 is blocked from entering into the nucleus, claudin 1 expression increases. Thus, it can be deduced that if NMT2 is allowed to enter into the nucleus, as is the case in the S38E line, then a decrease in claudin 1 expression can occur. The increased expression of claudin 1 in the S38A line may help explain why clumped growth patterns are observed. It is possible the blocking NMT2 from entering into the nucleus, by blocking phosphorylation of serine 38, may be preventing NMT2 from playing its normal role in regulation of the CLDN1 gene. This data revels a possible link between NMT2 regulation and cancer cell metastasis.

Example 6—Relevance of NMT1 in Clinical Outcome of ER Positive Breast Cancer

ER positive breast cancer cells develop resistance to SERMs partly due to activation of PI3K/Akt pathway. Recently, it has been demonstrated that activated mTOR is associated with better clinical outcome in primary tumors from an ERα positive cohort of breast cancer patients who were subsequently treated with tamoxifen (Shrivastav A et al., Breast Cancer Res 2014, 16(3):R49). Cytoplasmic and nuclear expression in above breast cancer cases was determined and an H score was given based on the intensity and percent positive cells for NMT1. Nuclear NMT1 predicted better recurrence free survival or recurrence free survival and death due to breast cancer.

FIG. 1 shows that high levels of nuclear NMT1 correspond to longer relapse free survival while low levels of both cytoplasmic and nuclear NMT1 correlate to shorter relapse free survival. As depicted in Table 1, patients with both low cytoplasmic and nuclear levels had a hazard ratio of 1.49 whereas patients with high levels of only nuclear NMT1 had the lowest hazard ratio 0.70. Patients with high cytoplasmic had a hazard ratio of 0.79 however this was not statistically significant. Together these data suggest that NMT1 could serve as a prognostic marker for predicting the possibility of recurrence.

Figure 2:
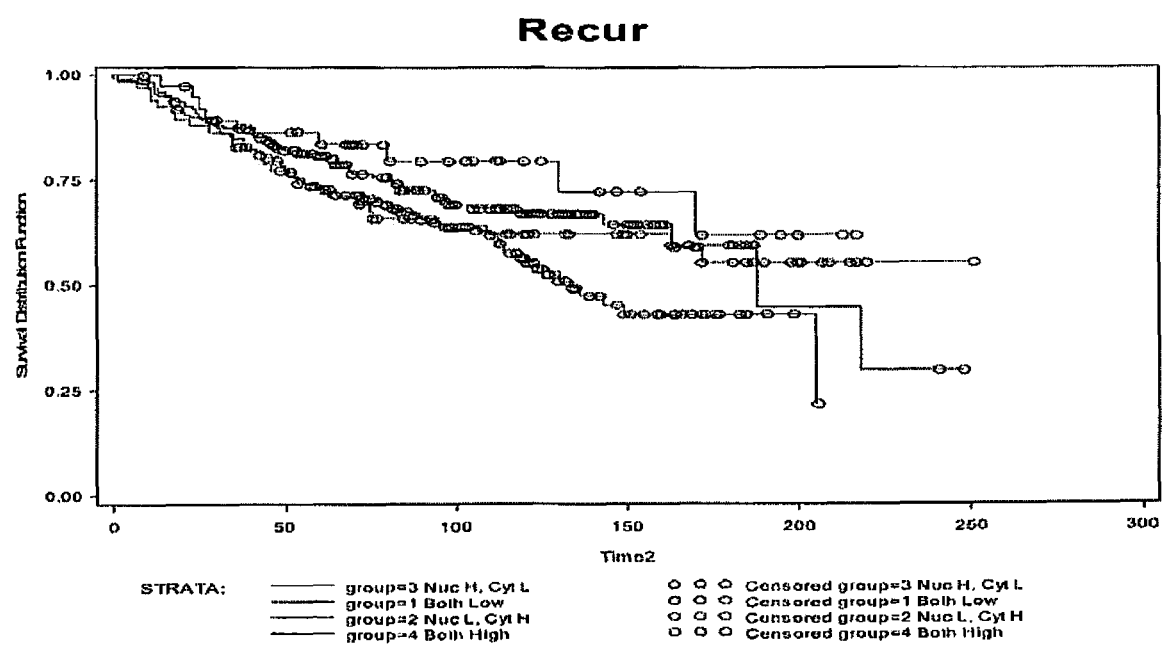
FIG. 2. High NMT1 nuclear levels correlate to longer reoccurrence free survival while both low cytoplasmic and nuclear levels of NMT1 are linked to higher chance of recurrence. Patients were separated into low or high categories based on the median H-score. Kaplan Meier curves were generated to assess whether any parameters associated with a significant change in patient survival. Recurrence analysis of low and high nuclear and cytoplasmic NMT1 levels.
Figure 3:
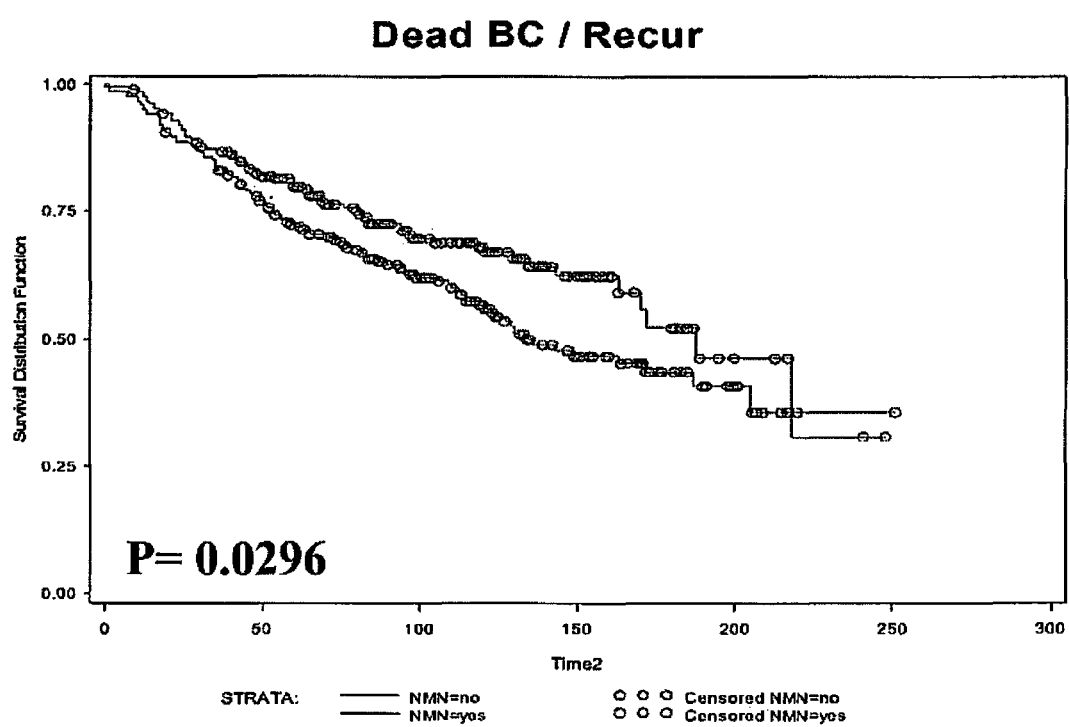
FIG. 3. Low NMT1 nuclear levels correlate with higher rate of death due to breast cancer or recurrence. Patients were separated into Low or High categories based on the median H-score. Kaplan Meier curves were generated to assess whether any parameters associated with a significant change in patient survival. Death due to breast cancer or recurrence analysis of low and high levels of nuclear NMT1.
Figure 4:
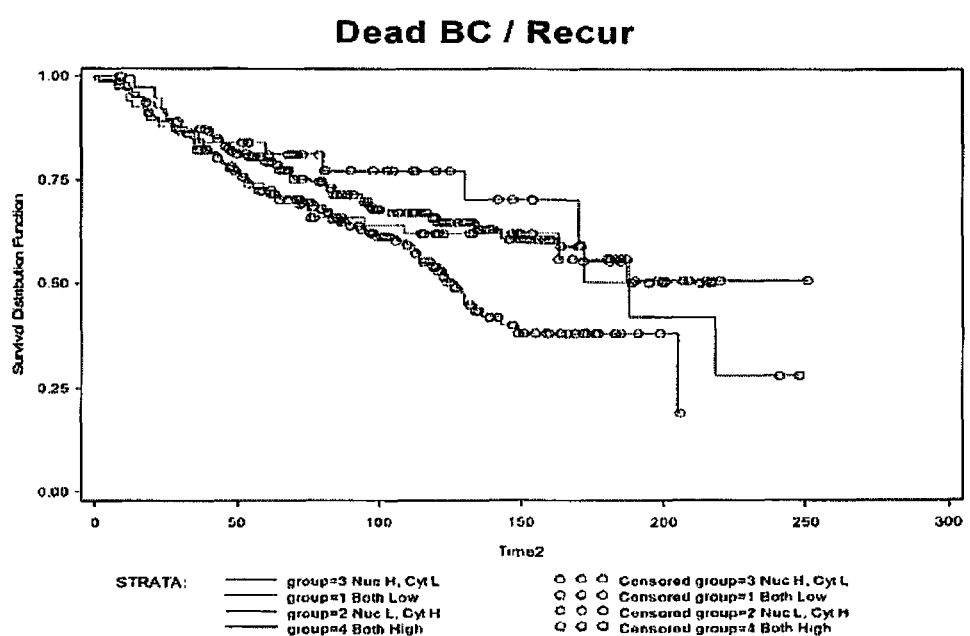
FIG. 4. Patients with high NMT1 nuclear levels were less likely to die due to breast cancer or recurrence. Patients separated into low or high categories based on the median H-score. Kaplan Meier curves were generated to assess whether any parameters associated with a significant change in patient survival. Recurrence analysis of low and high nuclear and cytoplasmic NMT1 levels.

In FIG. 2, it is evident that high levels of nuclear NMT1 are linked to lower levels of death due to breast cancer or recurrence.

Upon analysis of Table 2, it is evident that high levels of nuclear NMT1 had the lowest hazard ratio. As previously seen in the recurrence data, low levels of NMT1, be it cytoplasmic or nuclear, corresponded to high hazard ratios. The other data in the table was not statistically significant.

Three serine residues were identified that had high predictive scores for phosphorylation by either mTOR or the AKT isoforms. The serine 38 and 68 residues were predicted to be phosphorylated by mTOR and S258 by the three AKT isoforms. Interestingly, mTOR was the top ranked kinase to potentially phosphorylate S38, which is positionally analogous to S47 of NMT1. These serine residues are closest to the N-terminal end of the NLS common to both isozymes. This suggests that phosphorylation of the serine most proximal to the N-terminal end of the NLS of NMTs may be functionally conserved feature, despite the fact that the isoforms display sequence dissimilarity in the N-terminal regions.

Example 7—NMT1 and NMT2 Contain a Nuclear Localization Sequence (NLS)

Observation of a poly-lysine region within the two NMT proteins was notable as this sequence is indicative of an NLS (Kosugi, S., et al., J Biol Chem, 2009. 284(1): p. 478-85). Indeed, the NLStradamus software predicted that both NMT1 and NMT2 contain an NLS. The predicted NLS spans from K55 to K67 within NMT1 and from K46 to K58 within NMT2. The predicted NLSs constitute the same poly-lysine regions originally observed. This poly-lysine may be required for the binding of NMT1 to importin a, a nuclear pore protein that facilitates protein transport into the nucleus.

Example 8—NMT1—S47A/S47E-GFP

MCF7 cells expressing NMT1 with the S47A mutation expressed the GFP fusion protein exclusively in the cytoplasm. Interestingly, NMT1-S47A-GFP cells rapidly outgrew non-expressing cells under selection pressure of the G418 eukaryotic anti-biotic, constituting approximately 80% of the tissue culture surface area. Cells expressing cytoplasmic NMT1-S47E-GFP were remarkably lower in number compared to rapidly proliferating S47A counterparts under the same selection pressures, only proliferating at a rate that occupied approximately 5-10% of the cell culture surface area, with the remaining area consisting of non-transfected cells. A sub-population of cells expressed NMT1-S47E-GFP as 1-3 discernable spots overlapping the nuclear region of the cells, however, these fluorescence signals were subject to rapid photobleaching. Thus, it was difficult to quantify the overall population relative to cells expressing cytoplasmic fusion protein, or non-expressing cells.

Example 9—MCF7 Gene Expression of NMT and WT1 Regulated Genes Following Insulin Stimulation Growth conditions rich in serum growth factors and MCF7 cells with enhanced PI3K/AKT/mTOR activity both displayed increased NMT1-BASP1 interaction, with the latter exhibiting this interaction enhanced in the nucleus. NMT1 was also shown to bind to regions of DNA containing BASP1 regulated growth genes. Indeed, NMT1 and NMT2 expression showed little change following insulin or rapamycin treatment, suggesting that the PI3K/mTOR/AKT signalling pathway primarily regulates NMT1 and NMT2 through post-translational mechanisms. This supports our prediction that phosphorylation is the leading PI3K/AKT/mTOR mediated regulatory mechanism responsible for NMT1 modulation.

Example 10—Nuclear Localization Sequence (NLS) Identification

The nuclear import of NMT2 is aided by a nuclear transporter protein, importin, which escorts the target cargo protein through a nuclear pore complex into the nucleus.

Example 11—Differential Growth Rates of MCF7 and MCF7 NMT2 Mutant Expressing Cells In order to make ample stock of transfected MCF7 cells, they were cultured and expanded by incubating at 37° C. in 5% $CO_2$. However, during the cell culture it was noticed that MCF7-GFP-NMT2-S38A and MCF7-GFP-NMT2-S38E cells displayed very different proliferation rates compared to MCF7 and MCF7-GFP-NMT2 cells.

On day 1, the cells from each of the four lines were easily contained within the floor space of one 100/20 mm culture dish. All four of the lines were approximately 30-40% confluent. On day three, the MCF7, MCF7-GFP-NMT2, and S38E lines were split into three fresh culture dishes as the cells were confluent. The MCF7 and MCF7-GFP-NMT2 lines were approximately 80% confluent at the time of passaging and the S38E line was approximately 90% confluent. The S38A line was still at approximately 65% confluency. By day seven, the S38E line was confluent and had to be passaged again into four dishes. The MCF7 and MCF7-GFP-NMT2 lines were at approximately 65% confluency and so were not yet confluent enough to be passaged. Surprisingly, the S38A line was still not confluent in its original culture dish. The S38E cells appeared to be proliferating faster than the MCF7 and MCF7-GFP-NMT2 lines and much faster than the S38A line which appeared to be proliferating slower than the MCF7 and MCF7-GFP-NMT2 lines. These seemingly differing growth patterns warranted further investigation in the form of proliferation assays.

Example 12—Trypan Blue and Crystal Violet Proliferation Assays

Cellular proliferation rates were analyzed for MCF7, MCF7-GFP-NMT2, MCF7-GFP-NMT2-S38A and MCF7-GFP-NMT2-S38E cell lines using trypan blue and crystal violet proliferation assays. In the trypan blue assay (FIG. 5), at time point zero, all wells for all four cell lines contained approximately 50,000 cells.

At the 72-hour time point, the S38A cell line had proliferated to approximately 400,000 cells/ml while the MCF7 and MCF7-GFP-NMT2 control lines were at approximately 600,000 cells/ml. The S38E cell line had proliferated to approximately 1.1 million cells/ml. Between the 72- and 96-hour time points, the S38E cells rapidly became over confluent and started to undergo cell death due to lack of space to grow further and thus show a plateau in the curve. Due to the rapid proliferation of S38E cells, it became the rate limiting factor in carrying the assay post 96 h. At the 96-hour time point the S38E line was at approximately 1.25 million cells/ml while the S38A line was still only at approximately 500,000 thousand cells/ml.

The crystal violet assay (FIG. 6) relies on the amount of cell biomass (i.e. DNA), rather than the number of cells, as the dye binds to ribose sugars. The assay was performed in a 24 well plate with an equal number of cells (30,000) from each of four lines in each well. At time point zero, absorbance readings ranged from 0.24-0.42. Due to a dilution error, the S38A wells may have contained more than the intended 30,000 cells, and appeared to be approximately 20% more confluent in cell number (viewed under white light microscope) when compared to the wells of the other three cell lines which all appeared to contain approximately the same cell confluency. The S38A line had the highest absorbance rating of approximately 0.42 as a result of this dilution error. At the 96-hour time point, the S38A line had an absorbance reading of 1.63 nm while the S38E line had an absorbance rating of 3.74 nm. The two control lines showed a very similar proliferation rate throughout the assay. At the 96-hour time point the MCF7 line had an absorbance reading of 1.7 nm and the MCF7-GFP-NMT2 line had a reading of 2.3 nm.

Example 13—IGF1R Gene and Protein Expression Patterns

Dysregulation of the PI3K/Akt/mTOR pathway has been implicated in the development and progression of many types of cancer including ER+ breast cancer. The receptor tyrosine kinase transmembrane receptor responsible for the activation of this pathway is IGF1R. PhosphoNet software was used to determine the feasibility of the phosphorylation of NMT2, at position 38 and 68 serine residues, by mTOR, or any member, of the PI3K/Akt/mTOR pathway. Of the 500 human kinases analyzed by Phosphonet, mTOR received the highest kinase predictor V2 proximity score of 460, meaning that of the 500 kinases analyzed, mTOR is the most feasible for the phosphorylation of NMT2 at position 38. For the serine at position 68 mTOR did not receive a kinase predictor V2 proximity score. Interestingly, serine 68 was predicted to be phosphorylated by p70S6K protein, a downstream target of mTOR in the PI3K/Akt/mTOR pathway, with a kinase predictor proximity score of 1807.

RT-qPCR was performed to determine the status of IGF1R gene expression in MCF7, MCF7-GFP-NMT2, MCF7-GFP-NMT2-S38A and MCF7-GFP-NMT2-S38E cell lines (FIG. 23). The results show an under expression of IGF1R mRNA in S38A cells and an overexpression of IGF1R mRNA in S38E cells relative to the MCF7 control line.

Figure 8:
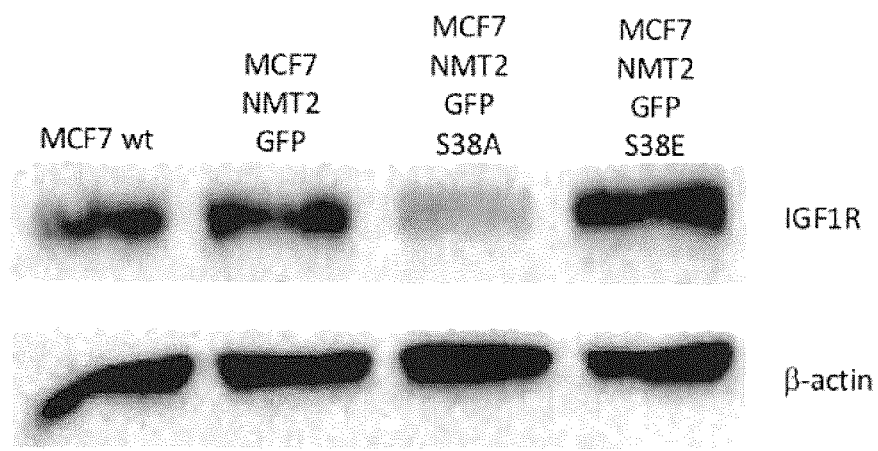
FIG. 8. Western blot PVDF membrane loaded with the four cell lines of interest and probed with anti-IGF1R and anti-p-actin.

IGF1R protein expression levels for all four lines were determined by Western blot analysis. The Western blot analysis of IGF1R is depicted in FIG. 8 (one of three Westerns which were performed for IGF1R protein expression analysis). All three independent experiments showed a similar pattern of expression for all four lines. The IGF1R protein expression levels obtained from these Western blots correlate closely with the pattern of expression shown in the previous IGF1R RT-qPCR chart. The Western blots show a very faint band of IGF1R protein expression in the S38A line while the RT-qPCR shows an under expression of IGF1R transcript in this line. A much stronger band of expression appears in the S38E line on the Western blot and the RT-qPCR displayed an overexpression of IGF1R transcript in this line.

The S38A cell line expressed a very low level of normalized IGF1R total protein while the S38E line expressed a high level IGF1R total protein.

Example 14—Localization of NMT2 in (A) MCF7 Cells and (B) MDA-MB 231

Figure 9A:
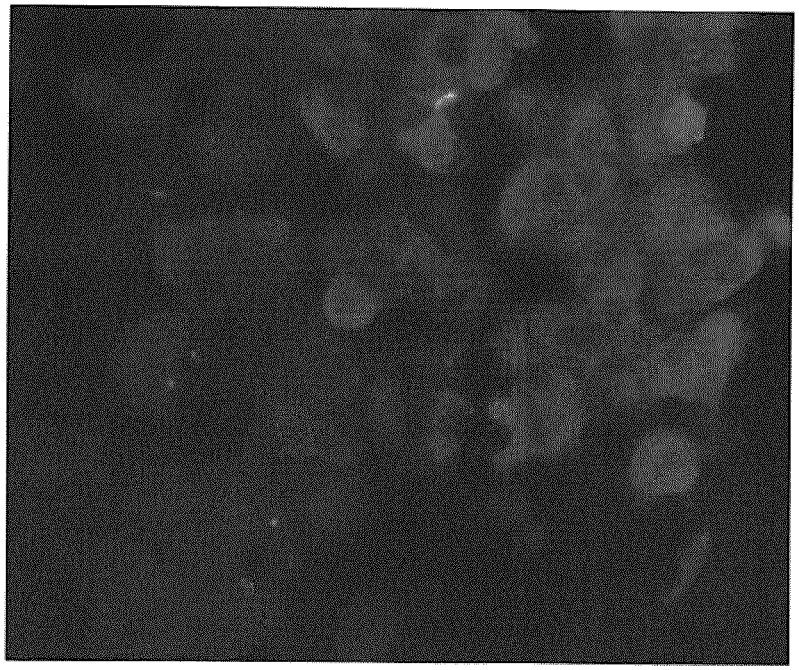
FIG. 9. Immunofluorescence images of NMT2 in (A) MCF7 cells and (B) MB-MDA 231.
Figure 9B:
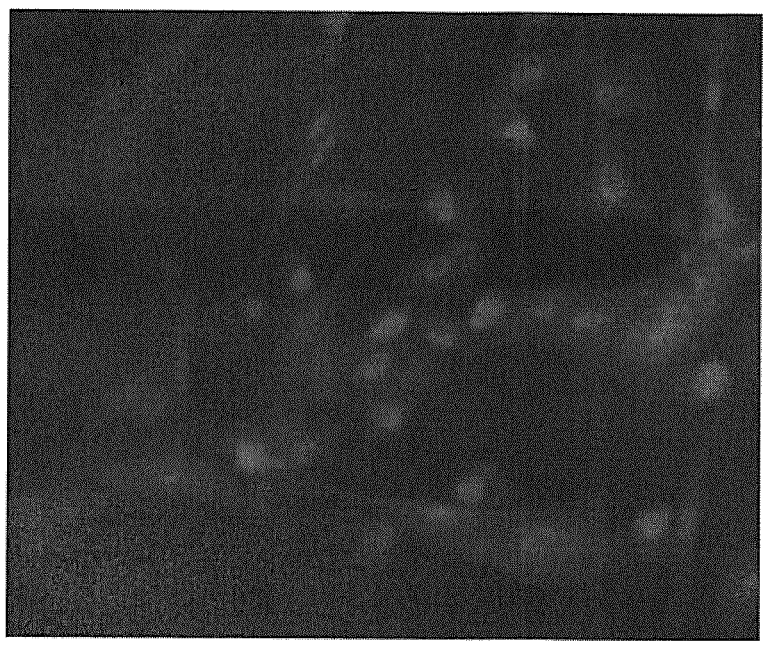
Figure 10:
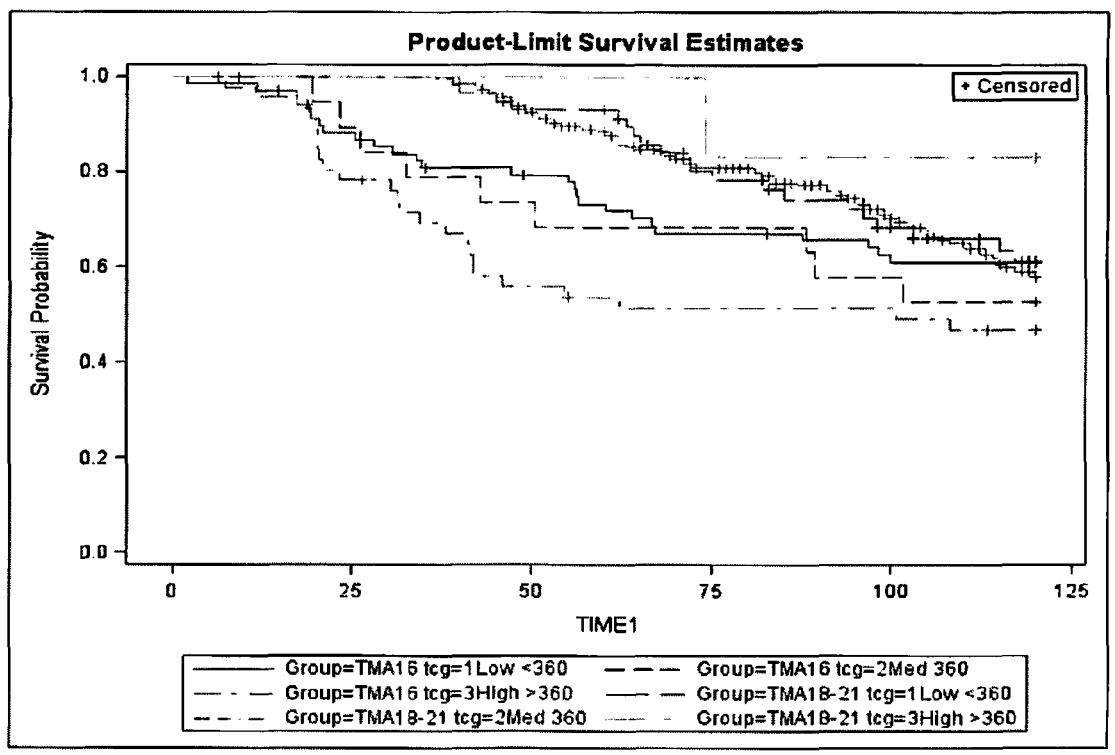
FIG. 10. TMA 16: Case with Triple Negative Breast Cancer; TMA 18-21 Cases with hormone receptor positive (ER, PR positive) or triple positive (ER, PR and Her2Neu). The patients were analyzed for their survival for the first 10 years. Cases are depicted with respect to the cytoplasmic expression of NMT2.
Figure 11:
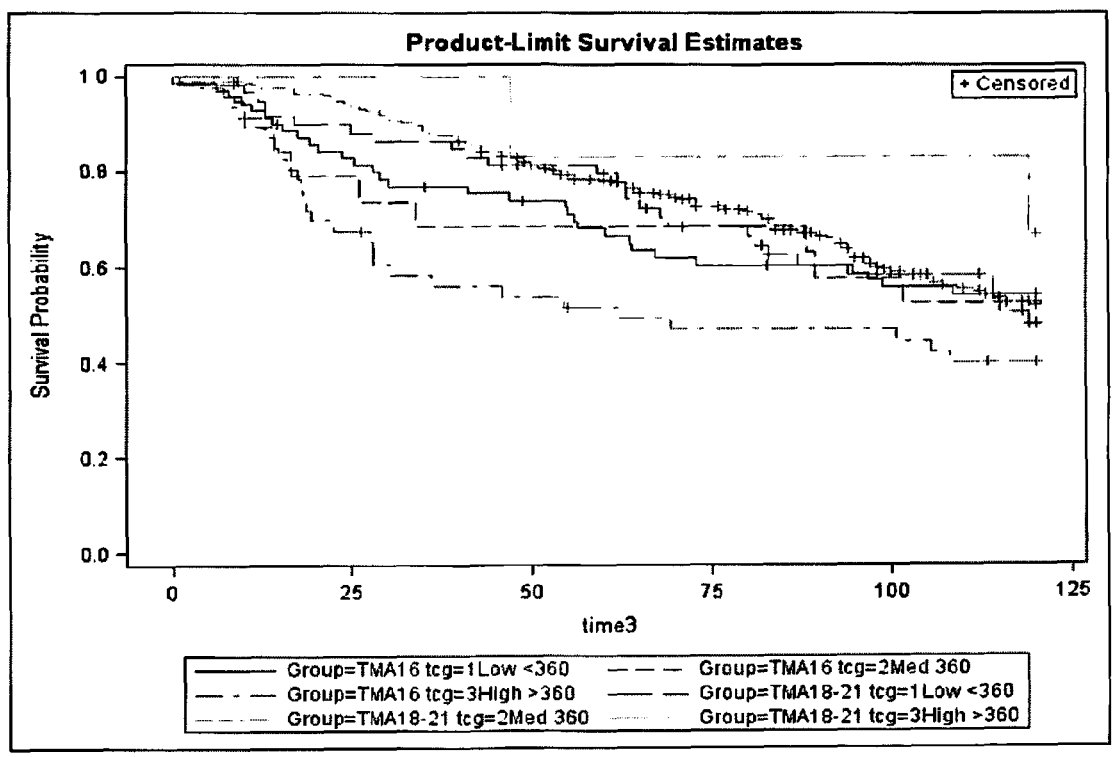
FIG. 11. TMA 16: Case with Triple Negative Breast Cancer; TMA 18-21 Cases with hormone receptor positive (ER, PR positive) or triple positive (ER, PR and Her2Neu). The patients were analyzed for their death or recurrence for the first 10 years. Cases are depicted with respect to the cytoplasmic expression of NMT2.
Figure 12:
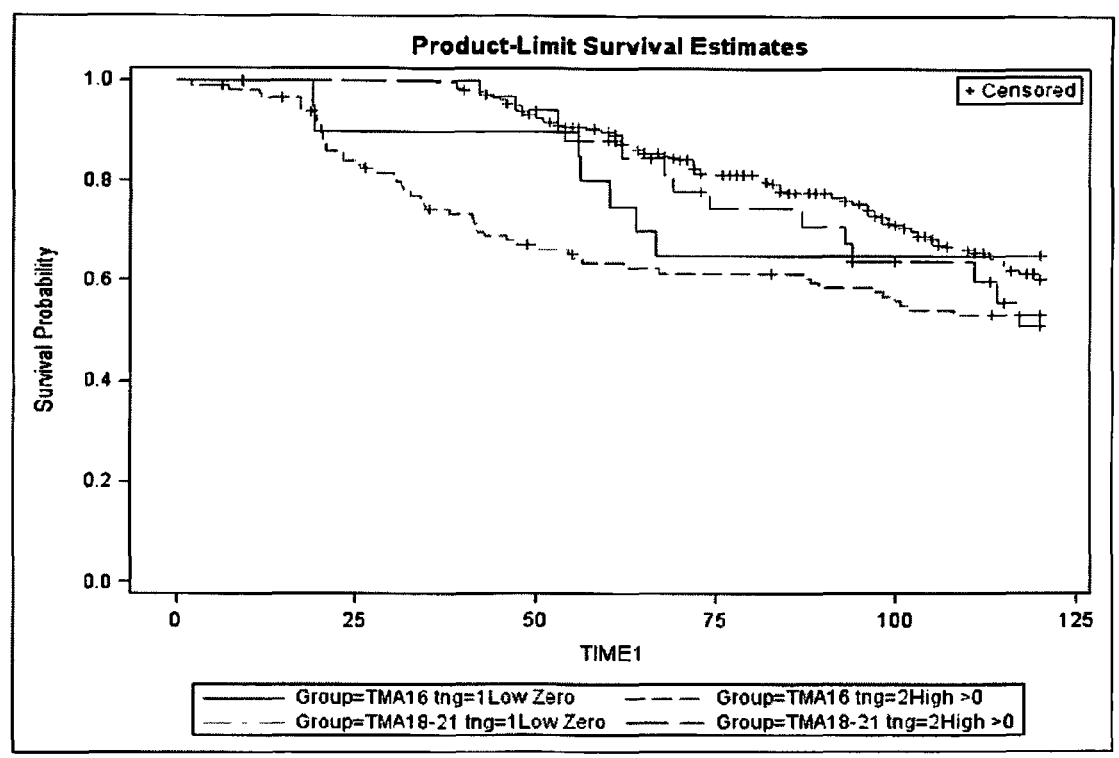
FIG. 12. TMA 16: Case with Triple Negative Breast Cancer; TMA 18-21 Cases with hormone receptor positive (ER, PR positive) or triple positive (ER, PR and Her2Neu). The patients were analyzed for their death or recurrence for the first 10 years. Cases are depicted with respect to the nuclear expression of NMT2 (no nuclear staining: Low zero. Positive nuclear staining: High zero).
Figure 13:
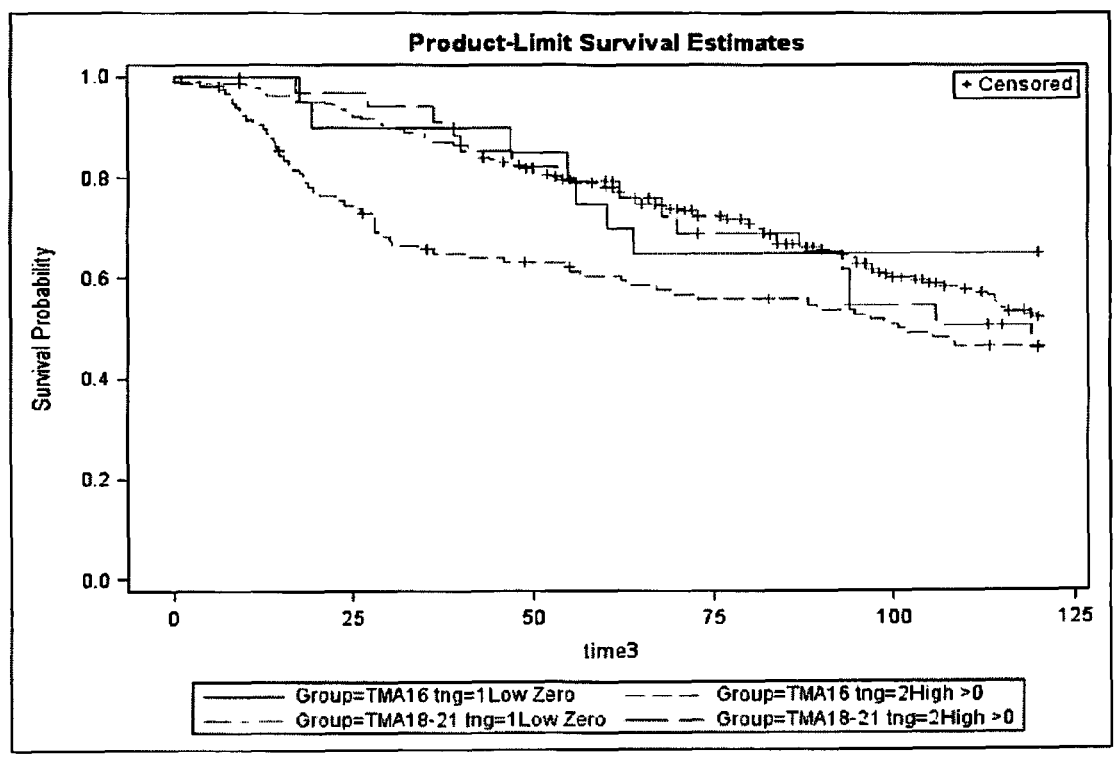
FIG. 13. TMA 16: Case with Triple Negative Breast Cancer; TMA 18-21 Cases with hormone receptor positive (ER, PR positive) or triple positive (ER, PR and Her2Neu). The patients were analyzed for their death or recurrence for the first 10 years. Cases are depicted with respect to the nuclear expression of NMT2 (no nuclear staining: Low zero. Positive nuclear staining: High zero).

With reference to FIGS. 9A and 9B, it can be seen that the expression of NMT2 was mostly observed in the cytoplasm of MCF7 cells. The MCF7 cell line was established from a pleural effusion at the Michigan Cancer Foundation. As the cells were originally derived from the metastases of an advanced tumor, the cell line is non-invasive. The MCF7 cells represents an early-stage disease because of the presence of functional ER and its dependence on estrogen for growth both in vitro and in vivo (JoEllen Welsh, Chapter 40—Animal Models for Studying Prevention and Treatment of Breast Cancer, Editor(s): P. Michael Conn, Animal Models for the Study of Human Disease, Academic Press, 2013, Pages 997-1018). In contrast, NMT2 was mostly localized in the nucleus of MDA-MB-231 cells. The MDA-MB-231 cell line was established from a pleural effusion of a patient with invasive ductal carcinoma. The MDA-MB-231 cells represents a late-stage disease. This cell line expresses mutated p53 and is ER, PR, and E-cadherin negative. These observations further validate the premise that nuclear NMT2 is potentially a hallmark feature of metastatic and invasive cancers.

Example 15—the Subcellular Localization of NMT1 in Hormone Positive and/or Her2Nue Positive Breast Cancers With reference to Tables 3-5 and FIGS. 10-13, it can be seen that the localization of NMT1 in the cytoplasm and/or nucleus in the primary breast cancer tissue provides the prognosis or the treatment response to endocrine therapy. The high expression of NMT1, semi-quantitatively determined by the "H" score, in the nucleus corresponds to a better prognosis, that is, with predicted better treatment outcomes when these patients later underwent endocrine therapy, whereas high cytoplasmic expression of NMT1 predicted poor prognosis and poor treatment response. Furthermore, both low cytoplasmic and low nuclear expression predicted worse prognosis and treatment response. As discussed herein, the status of the NMT1 expression will aid oncologists to identify the patients that were predicted to have poor prognosis and treatment response to due to the status of NMT1 in their breast cancer tissues. With this knowledge, the oncologists may put patients predicted to have poor prognosis and endocrine therapy response on regular surveillance and design treatment regimens that may include combination therapy or systemic chemotherapy to manage breast cancer and avoid recurrence.

Similarly, the localization of NMT2 in the nucleus is an indicator of highly invasive and metastatic breast cancer. The breast cancer tissues showing positive nuclear staining leads to poor survival. The nuclear localization of NMT2 was observed to be positive in cases of death due to breast cancer and recurrence. Most of the nuclear positive cases were observed in the triple negative breast cancer cohort, while survival from all the breast cancer types suggested poor outcome and recurrence in cases where the NMT2 was observed to be localised in the nucleus. High expression of cytoplasmic NMT2 also indicated poor prognosis and treatment outcomes with greater mortality even in those patients who survived for more than 10 years. As discussed herein, knowledge of the status of nuclear NMT2 in the primary breast cancer tissues would allow oncologists to design breast cancer treatment regimens wherein the nuclear NMT2 staining is positive. Specifically, breast cancer patients with nuclear NMT2 will be monitored more frequently and may be prescribed combination therapy that may include systemic chemotherapy. The status of NMT1 and NMT2 may be useful in deciding which hormone positive breast cancer patient should remain on endocrine therapy beyond five years rather than putting everyone on endocrine therapy for 10 years or more.

While the preferred embodiments of the invention have been described above, it will be recognized and understood that various modifications may be made therein, and the appended claims are intended to cover all such modifications which may fall within the spirit and scope of the invention.

TABLE 1

Univariate analysis of factors associated with recurrence free survival

| Single Predictor | Number | Hazard Ratio | 95% CI on HR | P |
|---|---|---|---|---|
| NMT1 Nucl >100 | 440 | 0.70 | 0.510 to 0.97 | 0.0304 |
| NMT1 Cyto >150 | 440 | 0.79 | 0.580 to 1.08 | 0.1347 |
| Both Nuclear & Cytoplasmic Low | 440 | 1.49 | 1.08 to 2.04 | 0.0014 |

TABLE 2

Univariate analysis of factors associated with death due to breast cancer or recurrence

| Single Predictor | Number | Hazard Ratio | 95% CI on HR | P |
|---|---|---|---|---|
| NMT1 Nucl >100 | 440 | 0.71 | 0.530 to 0.97 | 0.0306 |
| NMT1 Cyto >150 | 440 | 0.75 | 0.550 to 1.01 | 0.0543 |
| Both Nuclear & Cytoplasmic Low | 440 | 1.54 | 1.540 to 2.08 | 0.0055 |

TABLE 3

First 120 months

| Event Predictors | Death N | Event | P | Hazard Ratio | 95% Limits | Confidence |
|---|---|---|---|---|---|---|
| Cyto 16-21 | 437 | 160 | | | | |
| High >360 | | | 0.0284 | 1.72 | 1.06 | 2.81 |
| Med 360 | | | 0.6854 | 0.93 | 0.65 | 1.33 |
| Low <360 | | | reference | | | |
| Age at Dx | | | 0.0009 | 1.03 | 1.01 | 1.06 |
| Nuclear 16-21 | 437 | 160 | | | | |
| High >0 | | | 0.0006 | 1.74 | 1.27 | 2.39 |
| Low Zero | | | reference | | | |
| Age at Dx | | | 0.0002 | 1.04 | 1.02 | 1.06 |

| Event Predictors | Death or Recurr N | Event | P | Hazard Ratio | 95% Limits | Confidence |
|---|---|---|---|---|---|---|
| Cyto 16-21 | 437 | 192 | | | | |
| High >360 | | | 0.0657 | 1.52 | 0.97 | 2.38 |
| Med 360 | | | 0.3918 | 0.87 | 0.63 | 1.20 |
| Low <360 | | | reference | | | |
| Age at Dx | | | 0.0007 | 1.03 | 1.01 | 1.05 |
| Nuclear 16-21 | 437 | 192 | | | | |
| High >0 | | | 0.0027 | 1.56 | 1.17 | 2.09 |
| Low Zero | | | reference | | | |
| Age at Dx | | | 0.0002 | 1.03 | 1.02 | 1.05 |

TABLE 4 from 120 months onwards.

| Event Predictors | Death N | Event | P | Hazard Ratio | 95% Limits | Confidence |
|---|---|---|---|---|---|---|
| Cyto | 172 | 65 | | | | |
| High >360 | | | 0.89 | 1.06 | 0.48 | 2.35 |
| Med 360 | | | 0.009 | 2.15 | 1.21 | 3.82 |
| Low <360 | | | reference | | | |
| Age at Dx | | | <.0001 | 1.07 | 1.05 | 1.10 |
| Nuclear 16-21 | 172 | 65 | | | | |
| High >0 | | | 0.19 | 0.70 | 0.41 | 1.19 |
| Low Zero | | | reference | | | |
| Age at Dx | | | <.0001 | 1.07 | 1.04 | 1.09 |
| Cyto | 147 | 59 | | | | |
| High >360 | | | 0.68 | 0.82 | 0.33 | 2.07 |
| Med 360 | | | 0.0031 | 2.46 | 1.35 | 4.46 |
| Low <360 | | | reference | | | |
| Age at Dx | | | <.0001 | 1.08 | 1.05 | 1.12 |
| Nuclear | 147 | 59 | | | | |
| High >0 | | | 0.0366 | 0.55 | 0.31 | 0.96 |
| Low Zero | | | reference | | | |
| Age at Dx | | | <.0001 | 1.07 | 1.04 | 1.11 |

TABLE 5

Survival after Recurrence
All subjects who were used had a recurrence. Time = 0 at recurrence so the whole spectrum of data is used.

| Predictors | N | Event | P | Hazard Ratio | 95% Limits | Confidence |
|---|---|---|---|---|---|---|
| Cyto | 148 | 123 | | | | |
| High >360 | | | 0.031 | 1.85 | 1.06 | 3.25 |
| Med 360 | | | 0.71 | 1.08 | 0.71 | 1.65 |
| Low <360 | | | reference | | | |
| Age at Dx | | | 0.66 | 0.99 | 0.97 | 1.02 |

TABLE 5-continued

Survival after Recurrence
All subjects who were used had a recurrence. Time = 0
at recurrence so the whole spectrum of data is used.

| Nuclear | 148 | 123 | | | |
|---|---|---|---|---|---|
| High >0 | | | 0.0008 | 1.90 1.31 | 2.77 |
| Low Zero | | | reference | | |
| Age at Dx | | | 0.82 | 1.00 0.98 | 1.02 |

The invention claimed is:

1. A method of determining the prognosis of a breast cancer patient comprising:
   extracting a cell sample from a breast tumor of a patient;
   determining the cellular localization of NMT2 in at least one cell of the cell sample;
   wherein if the at least one cell of the cell sample is positive for nuclear NMT2, the prognosis is poor, and if the at least one cell of the cell sample is negative for nuclear NMT2, the prognosis is good.

2. The method according to claim 1 wherein a statistically significant number of cells are analyzed and the results are averaged.

3. The method according to claim 1 wherein, in a poor prognosis, a prognosis score for the hormone breast cancer patient is decreased.

4. The method according to claim 1 wherein in a good prognosis, a prognosis score for the hormone breast cancer patient is increased.

5. A method of determining the prognosis of a triple-negative breast cancer patient comprising:
   extracting a cell sample from a breast tumor of a patient;
   determining the cellular localization of NMT2 in at least one cell of the cell sample;
   wherein if the at least one cell of the cell sample shows positive nuclear localization of NMT2, the prognosis is poor.

6. The method according to claim 5 wherein a statistically significant number of cells are analyzed and the results are averaged.

7. The method according to claim 5 wherein, in a poor prognosis, a prognosis score for the hormone breast cancer patient is decreased.

8. The method according to claim 5 wherein in a good prognosis, a prognosis score for the hormone breast cancer patient is increased.

* * * * *